United States Patent [19]

Elbe et al.

[11] Patent Number: 6,054,473
[45] Date of Patent: Apr. 25, 2000

[54] 1,3-DIMETHYL-5-FLUORO-PYRAZOLE-4-CARBOXAMIDE DERIVATIVES, THEIR PREPARATION AND THEIR USE AS MICROBICIDES

[75] Inventors: Hans-Ludwig Elbe, Wuppertal; Dietmar Bielefeldt, Ratingen; Ralf Tiemann, Leverkusen; Stefan Dutzmann, Langenfeld; Klaus Stenzel, Düsseldorf; Martin Kugler, Leichlingen; Peter Wachtler, Krefeld, all of Germany

[73] Assignee: Bayer Aktiengesellschaft, Leverkusen, Germany

[21] Appl. No.: 09/230,160

[22] PCT Filed: Jul. 11, 1997

[86] PCT No.: PCT/EP97/03692

§ 371 Date: Jan. 20, 1999

§ 102(e) Date: Jan. 20, 1999

[87] PCT Pub. No.: WO98/03486

PCT Pub. Date: Jan. 29, 1998

[30] Foreign Application Priority Data

Jul. 24, 1996 [DE] Germany .................. 196 29 826

[51] Int. Cl.⁷ .......................... A01N 43/56; C07D 231/16
[52] U.S. Cl. .......................... 514/406; 548/374.1
[58] Field of Search .................. 548/374.1; 514/406

[56] References Cited

U.S. PATENT DOCUMENTS

| | | |
|---|---|---|
| 4,134,987 | 1/1979 | Huppatz . |
| 4,214,090 | 7/1980 | Huppatz . |
| 5,223,526 | 6/1993 | McLoughlin et al. . |
| 5,416,103 | 5/1995 | Eicken et al. . |

OTHER PUBLICATIONS

Chemical Abstracts, vol. 113, No. 1, Jul. 2, 1990, Abst. No. 73387c & JP 1990 85257.
Chemical Abstracts, vol. 109, No. 12/19/88, Abstract No. 231009v and JP 63,048,269 Feb. 29, 1988.

*Primary Examiner*—Robert W. Ramsuer
*Attorney, Agent, or Firm*—Joseph C. Gil; Carol Marmo

[57] ABSTRACT

The invention concerns 1,3-dimethyl-5-fluoro-pyrazole-4-carboxamides of formula (I) in which R stands for a group of formula(II) or (III), in which: $R^1$ stands for alkyl, cycloalkyl, bicycloalkyl, optionally substituted aryl or optionally substituted aralkyl; m stands for integers from 0 to 3 or two vicinal $R^1$ groups together stand for an alkylene chain with 3 or 4 carbon atoms; $R^2$ stands for alkyl, cycloalkyl, bicycloalkyl, optionally substituted aryl or optionally substituted aralkyl; and n stands for integers from 0 to 3 or two vicinal $R^2$ groups together stand for an alkylene chain with 3 or 4 carbon atoms. The invention further concerns a process for preparing the novel substances, and their use for combating undesirable micro-organisms for plant- and material-protection purposes.

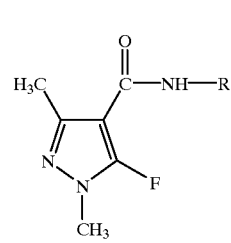

(I)

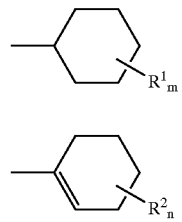

(II)

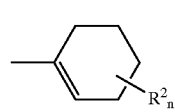

(III)

4 Claims, No Drawings

1,3-DIMETHYL-5-FLUORO-PYRAZOLE-4-CARBOXAMIDE DERIVATIVES, THEIR PREPARATION AND THEIR USE AS MICROBICIDES

TECHNICAL FIELD OF THE INVENTION

The present invention relates to novel 1,3-dimethyl-5-fluoro-pyrazol-4-carboxamides, to a process for their preparation and to their use as microbicides.

BACKGROUND OF THE INVENTION

It is already known that numerous pyrazol carboxamides have fungicidal properties (cf. WO 93-11 117 and EP-A 0 589 313). Thus, for example, N-(2-cycloheptyl)-1,3-dimethyl-5-fluoro-pyrazol-4-carboxanilide and N-(2-sec-butyl-cyclohexyl)-1,3-dimethylpyrazol-4-carboxamide can be employed for controlling fungi. The activity of these compounds is good, but leaves in some cases something to be desired at low application rates.

DETAILED DESCRIPTION OF THE INVENTION

This invention, accordingly, provides novel 1,3-dimethyl-5-fluoro-pyrazol-4-carboxamides of the formula

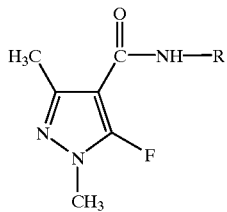

(I)

in which
R represents a grouping of the formula

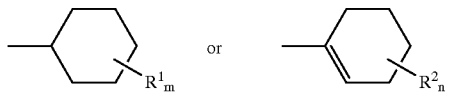

in which
R$^1$ represents alkyl, cycloalkyl, bicycloalkyl, optionally substituted aryl or optionally substituted aralkyl,
m represents integers from 0 to 3, or
two vicinal R$^1$ radicals together represent an alkylene chain having 3 or 4 carbon atoms,
R$^2$ represents alkyl, cycloalkyl, bicycloalkyl, optionally substituted aryl or optionally substituted aralkyl and
n represents integers from 0 to 3, or
two vicinal R$^2$ radicals together represent an alkylene chain having 3 or 4 carbon atoms.

Furthermore, it has been found that 1,3-dimethyl-5-fluoro-pyrazol-4-carboxamides of the formula (I) are obtained when 1,3-dimethyl-5-fluoro-pyrazol-4-carbonyl halides of the formula

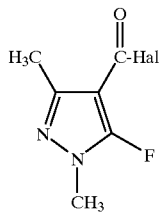

(II)

in which
Hal represents fluorine, chlorine or bromine,
are reacted with amines of the formula

in which
R is as defined above,
if appropriate in the presence of an acid binder and if appropriate in the presence of a diluent.

Finally, it has been found that the novel 1,3-dimethyl-5-fluoro-pyrazol-4-carboxamides of the formula (I) have very good microbicidal properties and can be used for controlling undesirable microorganisms, both in crop protection and in the protection of materials.

Surprisingly, the 1,3-dimethyl-5-fluoro-pyrazol-4-carboxamides of the formula (I) according to the invention have considerably better fungicidal activity than N-(2-cycloheptyl)-1,3-dimethyl-5-fluoro-pyrazol-4-carboxanilide and N-(2-sec-butylcyclohexyl)-1,3-dimethyl-pyrazol-4-carboxamide, which are constitutionally similar prior-art active compounds of the same direction of action.

The formula (I) provides a general definition of the 1,3-dimethyl-5-fluoro-pyrazol-4-carboxamides according to the invention.

R preferably represents a grouping of the formula

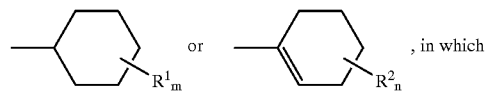

R$^1$ preferably represents a straight-chain or branched alkyl having 1 to 12 carbon atoms, cycloalkyl having 3 to 8 carbon atoms, bicycloalkyl having 7 to 12 carbon atoms, phenyl which is optionally mono- to trisubstituted by identical or different substituents selected from the group consisting of halogen and alkyl having 1 to 4 carbon atoms or represents phenylalkyl having 1 to 4 carbon atoms in the alkyl moiety which is optionally mono- to trisubstituted by identical or different substituents selected from the group consisting of halogen and alkyl having 1 to 4 carbon atoms,
m preferably represents the numbers 0, 1, 2 or 3, or
two vicinal R$^1$ radicals together represent an alkylene chain having 3 or 4 carbon atoms,
R$^2$ preferably represents a straight-chain or branched alkyl having 1 to 12 carbon atoms, cycloalkyl having 3 to 8 carbon atoms, bicycloalkyl having 7 to 12 carbon atoms, phenyl which is optionally mono- to trisubstituted by identical or different substituents selected from the group consisting of halogen and alkyl having 1 to 4 carbon atoms or represents phenylalkyl having 1 to 4 carbon atoms in the alkyl moiety which is optionally mono- to trisubstituted by identical or different substituents selected from the group consisting of halogen and alkyl having 1 to 4 carbon atoms and n represents the numbers 0, 1, 2 or 3, or two vicinal $R^2$ radicals together represent an alkylene chain having 3 or 4 carbon atoms.

Particular preference is given to 1,3-dimethyl-5-fluoro-pyrazol-4-carboxamides of the formula (I), in which R represents a grouping of the formula

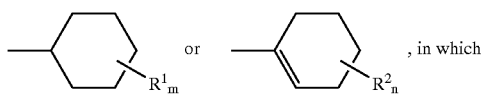

$R^1$ represents methyl, ethyl, n-propyl, isopropyl, n-butyl, sec-butyl, isobutyl, tert-butyl, 2-ethyl-butyl, octyl, decyl, dodecyl, cyclopropyl, cyclopentyl, cyclohexyl, cycloheptyl, cyclooctyl, bicyclo[2,2,1]heptyl, phenyl which is optionally mono- or disubstituted by fluorine, chlorine, bromine, methyl, ethyl, n-propyl, isopropyl and/or tert-butyl or represents phenylalkyl having 1 to 4 carbon atoms in the alkyl moiety, where the phenyl moiety may be mono- or disubstituted by fluorine, chlorine, bromine, methyl, ethyl, n-propyl, isopropyl and/or tert-butyl, m represents the numbers 0, 1, 2 or 3, where $R^1$ represents identical or different radicals if m represents 2 or 3, or two vicinal $R^1$ radicals together represent an alkylene chain having 3 or 4 carbon atoms, $R^2$ represents methyl, ethyl, n-propyl, isopropyl, n-butyl, sec-butyl, isobutyl, tert-butyl, 2-ethyl-butyl, octyl, decyl, dodecyl, cyclopropyl, cyclopentyl, cyclohexyl, cycloheptyl, cyclooctyl, bicyclo[2,2,1]heptyl, phenyl which is optionally mono- or disubstituted by fluorine, chlorine, bromine, methyl, ethyl, n-propyl, isopropyl and/or tert-butyl or represents phenylalkyl having 1 to 4 carbon atoms in the alkyl moiety, where the phenyl moiety may be mono- or disubstituted by fluorine, chlorine, bromine, methyl, ethyl, n-propyl, isopropyl and/or tert-butyl and n represents the numbers 0, 1, 2 or 3, where $R^2$ represents identical or different radicals if n represents 2 or 3, or two vicinal $R^2$ radicals together represent an alkylene chain having 3 or 4 carbon atoms.

Using 1,3-dimethyl-5-fluoro-pyrazol-4-carbonyl fluoride and 2-(2-ethyl-but- 1-yl)-cyclohexylamine as starting materials, the course of the process according to the invention can be illustrated by the equation below.

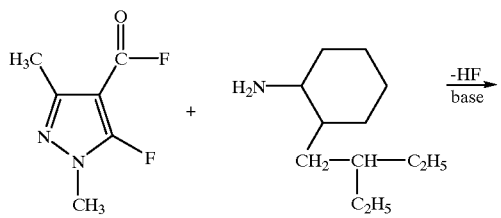

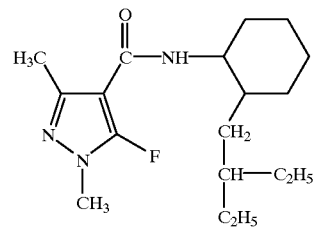

The formula (II) provides a general definition of the 1,3-dimethyl-5-fluoro-pyrazole-4-carbonyl halides required as starting materials for carrying out the process according to the invention. Hal also preferably represents fluorine, chlorine or bromine.

Some of the 1,3-dimethyl-5-fluoro-pyrazol-4-carbonyl halides are known (cf. WO 93-11 117). The 1,3-dimethyl-5-fluoro-pyrazol-4-carbonyl fluoride of the formula

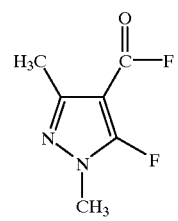

(II-1)

has hitherto not been disclosed. It can be prepared by reacting 1,3-dimethyl-5-chloro-pyrazol-4-carbonyl chloride of the formula

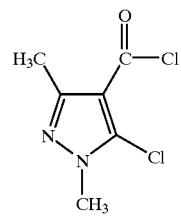

(IV)

with fluorides, if appropriate in the presence of a diluent.

The 1,3-dimethyl-5-chloro-pyrazol-4-carbonyl chloride of the formula (IV) required as starting material in the above process is known (cf. JP-A 1990-85 257 and Chem. Abstr. 113, 78 387).

Suitable reaction components for the process for preparing 1,3-dimethyl-5-fluoro-pyrazol-4-carbonyl fluoride of the formula (II-1) are all customary metal fluorides, ammonium fluoride and phosphonium fluorides. Preference is given to using alkali metal fluorides, such as potassium fluoride and caesium fluoride, furthermore ammonium fluoride or triphenylmethylphosphonium fluoride. The fluorides are known.

Suitable diluents for the preparation of the 1,3-dimethyl-5-fluoro-pyrazol-4-carbonyl fluoride of the formula (II-1) by the above process are all customary polar aprotic organic solvents. Preference is given to using ethers, such as diethyl ether, diisopropyl ether, methyl t-butyl ether, methyl t-amyl ether, dioxane, tetrahydrofuran, 1,2-dimethoxyethane, 1,2-diethoxyethane or anisol, furthermore ketones, such as acetone, butanone, methyl isobutyl ketone or cyclohexanone, furthermore nitriles, such as acetonitrile, propionitrile, n- or i-butyronitrile or benzonitrile; furthermore amides, such as N,N-dimethylformamide, N,N-dimethylacetamide, N-methylformanilide, N-methylpyrrolidone or hexamethylphosphoric triamide; furthermore esters, such as methyl acetate or ethyl acetate, and also sulphoxides, such as dimethyl sulphoxide, or sulphones, such as sulpholane.

The reaction temperatures in the above process for preparing 1,3-dimethyl-5-fluoro-pyrazol-4-carbonyl fluoride of the formula (II-1) can be varied within a relatively wide range. In general, the reaction is carried out at temperatures between 100 and 250° C., preferably between 150 and 200° C.

The preparation of 1,3-dimethyl-5-fluoro-pyrazol-4-carbonyl fluoride of the formula (II-1) by the above process is generally carried out under atmospheric pressure. However, it is also possible to carry out the reaction under elevated or reduced pressure.

In the preparation of the 1,3-dimethyl-5-fluoro-pyrazol-4-carbonyl fluoride of the formula (II-1) by the above process, generally 2 to 15 mol, preferably 2 to 4 mol, of fluoride are employed per mole of 1,3-dimethyl-5-chloro-pyrazol-4-carbonyl chloride of the formula (IV). Specifically, a solution of fluoride is generally admixed in a solvent with 1,3-dimethyl-5-chloro-pyrazol-4-carbonyl chloride, and the resulting mixture is heated at the required temperature until the reaction has ended. The subsequent work-up is carried out by customary methods. In general, the reaction mixture is subjected to a fractional distillation under reduced pressure.

The formula (III) provides a general definition of the amines required as reaction components for carrying out the process according to the invention. In this formula, R preferably has those meanings which have already been mentioned in connection with the description of the compounds of the formula (I) according to the invention as being preferred for this radical.

The amines of the formula (III) are known or can be prepared by known processes (cf. EP-A 0 529 313).

Suitable acid binders for carrying out the process according to the invention are all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to carry out the reaction without additional acid binder, or to employ an excess of the amine component so that it simultaneously acts as acid binder.

Suitable diluents for carrying out the process according to the invention are all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide, or sulphones, such as sulpholane.

When carrying out the process according to the invention, the reaction temperatures can be varied within a relatively wide range. In general, the reaction is carried out at temperatures between 0° C. and 100° C., preferably between 10° C. and 80° C.

The process according to the invention is generally carried out under atmospheric pressure. However, it is also possible to carry out the process under elevated or reduced pressure.

When carrying out the process according to the invention, generally 1 mol or else an excess of amine of the formula (III) and 1 to 3 mol of acid binder are employed per mole of 1,3-dimethyl-5-fluoro-pyrazol-4-carbonyl halide of the formula (II). However, it is also possible to employ the reaction components in other ratios. Work-up is carried out by customary methods. In general, the reaction mixture is admixed with water, the organic phase is separated off and, after drying, concentrated under reduced pressure. The residue that remains may, if required, be freed from any impurities that may still be present using customary methods, such as chromatography or recrystallization.

The compounds according to the invention have potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli;*

Pseudoperonospora cubensis;

Plasmopara species, such as, for example, *Plasmopara viticola;*

Bremia species, such as, for example, *Bremia lactucae;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis*;

Pyrenophora species, such as, for example, *Pyrenophora teres* or *P. graminea (conidia form: Drechslera, syn: Helminthosporium)*;

Cochliobolus species, such as, for example, *Cochliobolus sativus (conidia form: Drechslera, syn: Helminthosporium)*;

Uromyces species, such as, for example, *Uromyces appendiculatus*;

Puccinia species, such as, for example, *Puccinia recondita*;

Sclerotinia species, such as, for example, *Sclerotinia sclerotiorum*;

Tilletia species, such as, for example, *Tilletia caries*;

Ustilago species, such as, for example, *Ustilago nuda* or *Ustilago avenae*;

Pellicularia species, such as, for example, *Pellicularia sasakii*;

Pyricularia species, such as, for example, *Pyricularia oryzae*;

Fusarium species, such as, for example, *Fusarium culmorum*;

Botrytis species, such as, for example, *Botrytis cinerea*;

Septoria species, such as, for example, *Septoria nodorum*;

Leptosphaeria species, such as, for example, *Leptosphaeria nodorum*;

Cercospora species, such as, for example, *Cercospora canescens*;

Altemaria species, such as, for example, *Altemaria brassicae*; and

Pseudocercosporella species, such as, for example, *Pseudocercosporella herpotrichoides*.

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in viticulture and in fruit and vegetable growing, such as, for example, Venturia, Podosphaera, Phytophthora and Plasmopara species. They are also very successfully used for controlling rice diseases, such as, for example, Pyricularia species.

In the protection of materials, the compounds according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and boards, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds or compositions according to the invention preferably act against fungi, in particular moulds, wood-discolouring and wood-destroying fungi (Basidiomycetes) and against slime organisms and algae.

Microorganisms of the following genera may be mentioned as examples:

Alternaria, such as *Alternaria tenuis*,

Aspergillus, such as *Aspergillus niger*,

Chaetomium, such as *Chaetomium globosum*,

Coniophora, such as *Coniophora puetana*,

Lentinus, such as *Lentinus tigrinus*,

Penicillium, such as *Penicillium glaucum*,

Polyporus, such as *Polyporus versicolor*,

Aureobasidium, such as *Aureobasidium pullulans*,

Sclerophoma, such as *Sclerophoma pityophila*,

Trichoderma, such as *Trichoderma viride*,

Escherichia, such as *Escherichia coli*,

Pseudomonas, such as *Pseudomonas aeruginosa*, and

Staphylococcus, such as *Staphylococcus aureus*.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example ligno-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:
- aldimorph, ampropylfos, ampropylfos potassium, andoprim, anilazine, azaconazole, azoxystrobin,
- benalaxyl, benodanil, benomyl, benzamacril, benzamacryl-isobutyl, bialaphos, binapacryl, biphenyl, bitertanol, blasticidin-S, bromuconazole, bupirimate, buthiobate,
- calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
- debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
- edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
- guazatine,
- hexachlorobenzene, hexaconazole, hymexazole,
- imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
- kasugamycin, kresoxim-methyl, copper preparations, such as: copper hydroxide, copper naphthenate, copper oxychloride, copper sulphate, copper oxide, oxine-copper and Bordeaux mixture,
- mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
- nickel dimethyldithiocarbamate, nitrothal-isopropyl, nuarimol,
- ofurace, oxadixyl, oxamocarb, oxolinic acid, oxycarboxim, oxyfenthiin,
- paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
- quinconazole, quintozene(PCNB),
- sulphur and sulphur preparations,
- tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichiamide, tricyclazole, tridemorph, triflumizole, triforine, triticonazole,
- uniconazole,
- validamycin A, vinclozolin, viniconazole,
- zarilamide, zineb, ziram and also
- Dagger G,
- OK-8705,
- OK-8801,
- 2',6'-dibromo-2-methyl-4'-trifluoromethoxy-4'-trifluoromethyl-1,3-thiazole-5-carboxanilide,
- 2,6-dichloro-N-(4-trifluoromethylbenzyl)-benzamide,
- 2-aminobutane,
- 2-phenylphenol (OPP),
- 8-hydroxyquinoline sulphate,
- cis-1-(4-chlorophenyl)-2-(1H-1,2,4-triazol-1-yl)-cycloheptanol,
- (5RS,6RS)-6-hydroxy-2,2,7,7-tetramethyl-5-(1H-1,2,4-triazol-1-yl)-3-octanone,
- α-(2,4-dichlorophenyl)-β-methoxy-α-methyl-1H-1,2,4-triazole-1-ethanol,
- α-(1,1-dimethylethyl)-β-(2-phenoxyethyl)-1H-1,2,4-triazole-1-ethanol,
- 1-[1-[2-[(2,4-dichlorophenyl)-methoxy]-phenyl]-ethenyl]-1H-imidazole,
- bis-(1-methylethyl)-3-methyl-4-[(3-methylbenzoyl)oxy]-2,5-thiophenedicarboxylate,
- 2,6-dichloro-N-[[4-(trifluoromethyl)-phenyl]-methyl]-benzamide,
- (E)-α-(methoxyimino)-N-methyl-2-phenoxy-phenylacetamide,
- 9H-xanthene-2-[(phenylamino)-carbonyl]-9-carboxylic hydrazide,
- O-methyl S-phenyl phenylpropylphosphoramidothioate,
- N-(5-chloro-2-methylphenyl)-2-methoxy-N-(2-oxo-3-oxazolidinyl)-acetamide,
- 1-(2,4-dichlorophenyl)-2-(1H-1,2,4-triazol-1-yl)ethanone-O-(phenylmethyl)-oxime,
- N-(2,6-dimethylphenyl)-2-methoxy-N-(tetrahydro-2-oxo-3-thienyl)-acetamide,
- cis-4-[3-[4-(1,1-dimethylpropyl)-phenyl-2-methylpropyl]-2,6-dimethylmorpholinehydrochloride,
- 1-(3,5-dichlorophenyl)-3-(2-propenyl)-2,5-pyrrolidindione, 1-methyl-5-nonyl-2-(phenylmethyl)-3-pyrrolidinole,
1-[[2-(4-chlorophenyl)-3-phenyloxiranyl]-methyl]-1H-1, 2,4-triazole, methanetetrathiol sodium salt,
2-(2,3,3-triiodo-2-propenyl)-2H-tetrazole,
N-[3-chloro-4,5-bis(2-propinyloxy)-phenyl]-N'-methoxy-methanimidamide,
α-(5-methyl-1,3-dioxan-5-yl)-β-[[4-(trifluoromethyl)-phenyl]-methylene]-1H-1,2,4-triazole-1-ethanol,
1-(2-methyl-1-naphthalenyl)-1H-pyrrol-2,5-dione,
N-(-2,6-dimethylphenyl)-2-methoxy-N-(tetrahydro-2-oxo-3-furanyl)-acetamide,
3,4-dichloro-1-[4-(difluoromethoxy)-phenyl]-1H-pyrrol-2,5-dione,
N-[2,2,2-trichloro-1-[(chloroacetyl)-amino]-ethyl]-benzamide,
N-formyl-N-hydroxy-DL-alanine sodium salt,
N-(4-cyclohexylphenyl)-1,4,5,6-tetrahydro-2-pyrimidinamine,
4-methyl-tetrazolo[1,5-a]quinazolin-5(4H)-one,
2-chloro-N-(2,6-dimethylphenyl)-N-(isothiocyanatomethyl)-acetamide,
ethyl [(4-chlorophenyl)-azo]-cyanoacetate,
N-(4-hexylphenyl)-1,4,5,6-tetrahydro-2-pyrimidinamine,
N-(2-chloro-4-nitrophenyl)-4-methyl-3-nitro-benzenesulfonamide,
methyl N-(chloroacetyl)-N-(2,6-dimethylphenyl)-DL-alaninate,
3-[2-(4-chlorophenyl)-5-ethoxy-3-isoxazolidinyl]-pyridine,
2-[(1-methylethyl)sulphonyl]-5-(trichloromethyl)-1,3,4-thiadiazole,
spiro[2H]-1-benzopyrane-2,1'(3'H)-isobenzofuran]-3'-one,
methyl N-(2,6-dimethylphenyl)-N-(5-isoxazolylcarbonyl)-DL-alaninate, potassium hydrogen carbonate,
1-[[2-(2,4-dichlorophenyl)-1,3-dioxolan-2-yl]-methyl]-1H-imidazole,
1-[(diiodomethyl)-sulphonyl]-4-methyl-benzene,
2-bromo-2-(bromomethyl)-pentanedinitrile,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
methyl 1-(2,3-dihydro-2,2-dimethyl-1H-inden- 1-yl)-1H-imidazole-5-carboxylate,
2-chloro-N-(2,3-dihydro-1,1,3-trimethyl-1H-inden-4-yl)-3-pyridinecarboxamide,
O,O-diethyl [2-(dipropylamino)-2-oxoethyl]-ethylphosphoramidothioate,
α-(2,4-dichlorophenyl)-β-fluoro-β-propyl-1H-1,2,4-triazole-1-ethanol,
3-(1,1-dimethylpropyl-1-oxo-1H-indene-2-carbonitrile,
2,6-dichloro-5-(methylthio)-4-pyrimidinyl-thiocyanate,
S-methyl 1,2,3-benzothiadiazole-7-carbothioate,
N-(6-methoxy)-3-pyridinyl)-cyclopropanecarboxamide,
3,5-dichloro-N-[cyano-[(1-methyl-2-propynyl)-oxy]-methyl]-benzamide,
4-chloro-2-cyano-N,N-dimethyl-5-(4-methylphenyl)-1H-imidazole-1-sulfonamide,
8-(1,1-dimethylethyl)-N-ethyl-N-propyl-1,4-dioxaspiro [4.5]decane-2-methanamine,
2,2-dichloro-N-[1-(4-chlorophenyl)-ethyl]-1-ethyl-3-methyl-cyclopropanecarboxamide,
N-(2,3-dichloro4-hydroxyphenyl)-1-methyl-cyclohexanecarboxamide.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, betacyluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992 salithion, sebufos, silafluofen, sulfotep, sulprofos, tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensis, tralomethrin, triarathen, triazophos, triazuron, trichlorfon, triflumuron, trimethacarb, vamidothion, XMC, xylylcarb, zetamethrin.

It is also possible to admix other known active compounds, such as herbicides, fertilizers and growth-promoting substances.

The active compounds can be used as such or in the form of their formulations or the use forms prepared therefrom, such as ready-to-use solutions, suspensions, wettable powders, pastes, soluble powders, dusts and granules. They are used in the customary manner, for example by pouring, spraying, atomizing, scattering, dusting, foaming, brushing on and the like. It is further possible to apply the active compounds by the ultra-low volume method or to inject the active compound formulation, or the active compound itself, into the soil. The seed of the plants can also be treated.

In the treatment of parts of plants, the active compound concentrations in the use forms can be varied within a relatively wide range. They are, in general, between 1 and 0.0001% by weight, preferably between 0.5 and 0.001% by weight. In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

The compositions used for the protection of industrial materials generally comprise an amount of 1 to 95%, preferably 10 to 75%, of the active compounds.

The use concentrations of the active compounds according to the invention depend on the species and the occurrence of the microorganisms to be controlled and on the composition of the material to be protected. The optimal rate of application can be determined by test series. In general, the use concentrations are in the range from 0.001 to 5% by weight, preferably 0.05 to 1.0% by weight, based on the material to be protected.

The activity and the activity spectrum of the active compounds to be used according to the invention in the protection of materials, or of the compositions, concentrates or, very generally, formulations which can be prepared therefrom, can be increased by adding, if appropriate, other antimicrobially active compounds, fungicides, bactericides, herbicides, insecticides or other active compounds to widen the activity spectrum or to achieve particular effects, such as, for example, additional protection against insects. These mixtures may have a wider activity spectrum than the compounds according to the invention.

The preparation and the use of the active compounds according to the invention is illustrated by the examples below.

PREPARATION EXAMPLES

EXAMPLE 1

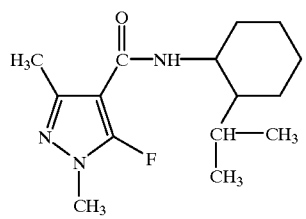

At room temperature, a solution of 2.6 g (0.015 mol) of 5-fluoro-1,3-dimethyl-pyrazol-4-carbonyl chloride in 10 ml of toluene is added dropwise with stirring to a mixture of 2.1 g (0.015 mol) of 2-isopropyl-cyclohexylamine, 1.5 g (0.015 mol) of triethylamine and 40 ml of toluene. After the addition has ended, the reaction mixture is stirred at room temperature for another 2 hours and then admixed with water. The organic phase is separated off, dried over sodium sulphate and concentrated under reduced pressure. The residue that remains is stirred with n-hexane. The resulting solid product is filtered off with suction and dried. In this manner, 3.6 g (85.4% of theory) of N-(2-isopropyl)-cyclohexyl-5-fluoro-1,3-dimethyl-pyrazole-4-carboxamide are obtained. m.p. 126° C.

The 1,3-dimethyl-5-fluoro-pyrazol-4-carboxamides of the formula (I) listed in the table below are prepared in a similar manner.

TABLE 1

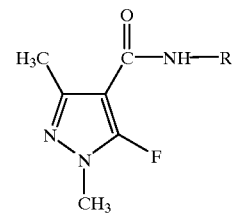

(I)

| Example No. | R | Physical constant |
|---|---|---|
| 2 | CH₂—CH(C₂H₅)—cyclohexyl, C₂H₅ | ¹H-NMR*) δ=2.44(s, 3H) |
| 3 | cyclohexyl—C₁₂H₂₅ | ¹H-NMR*) δ=3.60(s, 3H) |
| 4 | H₅C₂—cyclohexyl—CH₃ | m.p. 78° C. |
| 5 | cyclohexyl—C₂H₅ | m.p. 107° C. |
| 6 | cyclohexyl(CH₃)—cyclohexyl | m.p. 173° C. |
| 7 | H₃C, H₃C—cyclohexyl—CH₃ | m.p. 155° C. |

TABLE 1-continued (I)

Structure: 3-methyl-5-fluoro-1-methyl-1H-pyrazole-4-carboxamide with NH—R substituent

| Example No. | R | Physical constant |
|---|---|---|
| 8 | 2-methyl-1,3-bis(iso-C$_3$H$_7$)cyclohexyl | $^1$H-NMR*) δ=3.69(s, 3H) |
| 9 | 3,4-dimethyl-(4-tert-butyl)cyclohexyl (diastereomers) | m.p. 126° C. |
| 10 | 3-ethyl-2-methyl-4-methyl-(5-C$_2$H$_5$)cyclohexyl | m.p. 167° C. |
| 11 | bicyclohexyl | m.p. 177° C. |
| 12 | 4-(2-phenylpropan-2-yl)cyclohexyl | $^1$H-NMR*) δ=3.67(s, 3H) |
| 13 | 4-methylcyclohexyl | m.p. 116° C. |
| 14 | 2,4,6-trimethylcyclohexyl (diastereomers) | m.p. 129° C. |
| 15 | 2-methyl-3,5-diethylcyclohexyl | m.p. 98° C. |
| 16 | cyclohexyl | m.p. 147–148° C. |
| 17 | 2,5-dimethyl-(3-methyl)cyclohexyl (menthyl form) | m.p. 176–177° C. |
| 18 | 3,5-dimethylcyclohexyl (iso-form) | m.p. 96–98° C. |
| 19 | 2,3-dimethylcyclohexyl | m.p. 119–122° C. |
| 20 | 2,3-dimethyl-(4-methyl)cyclohexyl (iso-form) | m.p. 137° C. |
| 21 | 2-methyl-(sec-butyl)cyclohexyl (diastereomer A) | $^1$H-NMR*) δ=3.71(s, 3H) |

TABLE 1-continued (I) Structure: pyrazole with H3C at 3-position, C(=O)-NH-R at 4-position, F at 5-position, N-CH3 at 1-position.

| Example No. | R | Physical constant |
|---|---|---|
| 22 | 2-methylcyclohexyl-CH(CH3)-C2H5 (diastereomer B) | $^1$H-NMR*) δ=3.62(s, 3H) |
| 23 | cyclohexyl with C2H5, C2H5 substituents | m.p. 140° C. |
| 24 | cyclohexyl with methyl and C2H5 substituents | m.p. 163–164° C. |
| 25 | methylcyclohexyl fused with bicyclic system | m.p. 146° C. |
| 26 | cyclohexyl with methyl and CH3 substituents | m.p. 139–141° C. |
| 27 | methylcyclohexyl-CH(CH3)-C2H5 (diastereo mixture) | $^1$H-NMR*) δ=2.45(s, 3H) |
| 28 | decahydronaphthyl (methyl-substituted) | m.p. 139° C. |
| 29 | cyclohexyl with CH3, CH3, CH3 substituents | m.p. 91° C. |

*) The $^1$H-NMR-spectra were recorded in deuterochloroform (CDCl$_3$) using tetramethylsilane (TMS) as internal standard. Stated is in each case the chemical shift as δ value in ppm.

USE EXAMPLES

EXAMPLE A

Erysiphe Test (barley)/Protective

Solvent: 10 parts by weight of N-methyl-pyrrolidone
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are dusted with spores of Erysiphe graminis f.sp. hordei.

The plants are placed in a greenhouse at a temperature of approximately 20° C. and a relative atmospheric humidity of approximately 80% to promote the development of mildew pustules.

Evaluation is carried out 7 days after the inoculation. 0% means an efficacy which corresponds to that of the untreated control, whereas an efficacy of 100% means that no infection is observed.

Active compounds, application rates and test results are shown in the table below.

TABLE A

Erysiphe test (barley)/protective

| Active compound | Application rate of active compound in g/ha | Efficacy in % |
|---|---|---|
| According to the invention: | 250 | 100 |

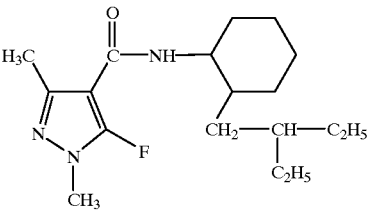

(2)

EXAMPLE B

Pyrenophora Teres Test (barley)/Protective

Solvent: 10 parts by weight of N-methyl-pyrrolidone
Emulsifier: 0.6 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate.

After the spray coating has dried on, the plants are sprayed with a conidia suspension of Pyrenophora teres.

The plants remain in an incubation cabin at 20° C. and 100% relative atmospheric humidity for 48 hours.

The plants are placed in a greenhouse at a temperature of approximately 20° C. and a relative atmospheric humidity of approximately 80%.

Evaluation is carried out 7 days after the inoculation. 0% means an efficacy which corresponds to that of the untreated control, while an efficacy of 100% means that no infection is observed.

Active compounds, application rates and test results are shown in the table below.

TABLE B

Pyrenophora teres test (barley)/protective

| Active compound | Application rate of active compound in g/ha | Efficacy in % |
|---|---|---|
| According to the invention: | 125 | 100 |

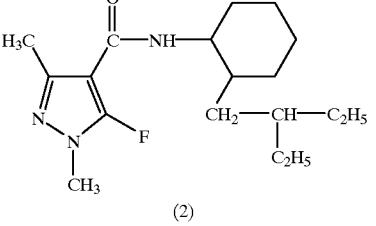

(2)

EXAMPLE C

Material Protection Test

To assess the antifungal activity, the minimum inhibitory concentrations (MICs) of the compounds according to the invention are determined:

An agar which is prepared using malt extract is admixed with active compounds according to the invention at concentrations of from 0.1 mg/l to 5,000 mg/l. When the agar has set, it is contaminated with pure cultures of test organisms. The samples are stored for 2 weeks at 28° C. and 60 to 70% relative atmospheric humidity, after which the minimum inhibitory concentration (MIC) is determined. The MIC is the lowest concentration of active compound at which no colonization of the microbe species used occurs.

Active compounds and test results are shown in the table below.

TABLE C

Material protection test
Minimum inhibitory concentration (MIC) in mg/l

| Test organism | Active compound of Example No. 16 | Active compound of Example No. 19 |
|---|---|---|
| Chaetomium globosum | 100 | 100 |
| Aspergillus niger | 200 | 400 |

EXAMPLE D

Sphaerotheca Test (cucumber)/Protective

Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

Evaluation is carried out 10 days after the inoculation. 0% means an efficacy which corresponds to that of the control, while an efficacy of 100% means that no infection is observed.

Active compounds, application rates and test results are shown in the table below.

TABLE D

Sphaerotheca test (cucumber)/protective

| Active compound | Application rate of active compound in g/ha | Efficacy in % |
|---|---|---|
| Known form EP-A 0 589 313: | 100 | 63 |

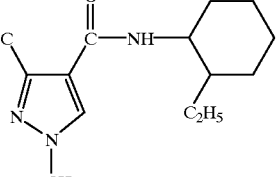

TABLE D-continued

Sphaerotheca test (cucumber)/protective

| Active compound | Application rate of active compound in g/ha | Efficacy in % |
|---|---|---|
| According to the invention: | | |
| 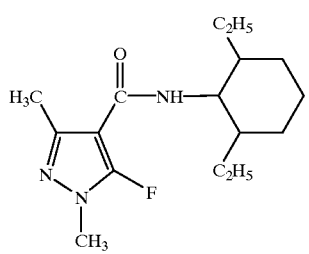 (23) | 100 | 87 |
| 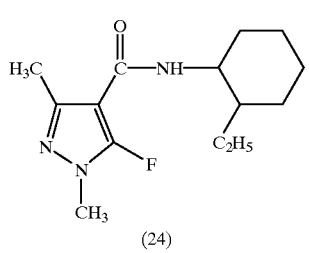 (24) | 100 | 86 |
| 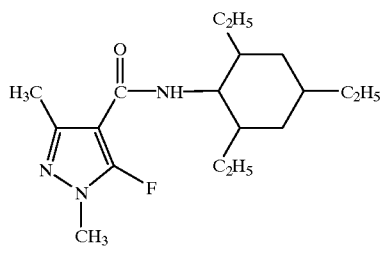 (15) | 100 | 87 |
| 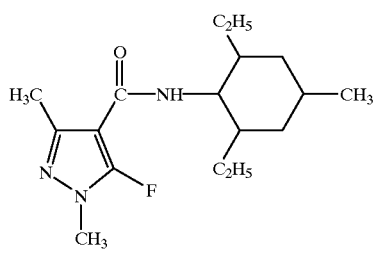 (10) | 100 | 100 |

EXAMPLE E
Venturia Test (apple)/Protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the causative organism of apple scab Venturia inaequalis and then remain in an incubation cabin at approximately 20° C. and 100% relative atmospheric humidity for 1 day.

The plants are then placed in a greenhouse at approximately 21° C. and a relative atmospheric humidity of approximately 90%.

Evaluation is carried out 12 days after the inoculation. 0% means an efficacy which corresponds to that of the control, while an efficacy of 100% means that no infection is observed.

Active compounds, application rates and test results are shown in the table below.

TABLE E

Ventruia test (apple)/protective

| Active compound | Application rate of active compound in g/ha | Efficacy in % |
|---|---|---|
| Known from EP-A 0 589 313: | | |
| 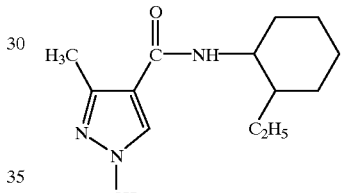 | 100 | 0 |
| According to the invention: | | |
| 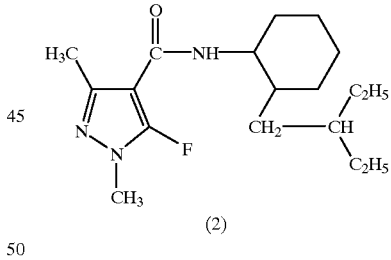 (2) | 100 | 91 |
| 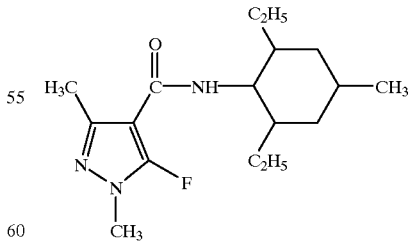 (10) | 100 | 95 |

What is claimed is:

1. A 1,3-dimethyl-5-fluoro-pyrazol-4-carboxamide of the formula

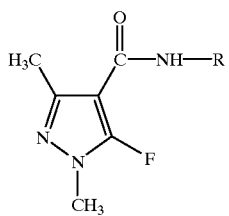

(I)

in which
R represents a grouping of the formula

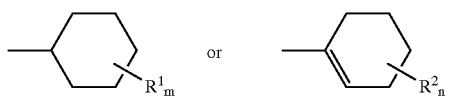

in which
- $R^1$ represents a straight-chain or branched alkyl having 1 to 12 carbon atoms, cycloalkyl having 3 to 8 carbon atoms, bicycloalkyl having 7 to 12 carbon atoms, phenyl which is optionally mono- to trisubstituted by identical or different substituents selected from the group consisting of halogen and alkyl having 1 to 4 carbon atoms or represents phenylalkyl having 1 to 4 carbon atoms in the alkyl moiety which is optionally mono- to trisubstituted by identical or different substituents selected from the group consisting of halogen and alkyl having 1 to 4 carbon atoms,
- m represents the numbers 0, 1, 2 or 3, or two vicinal $R^1$ radicals together represent an alkylene chain having 3 or 4 carbon atoms,
- $R^2$ represents a straight-chain or branched alkyl having 1 to 12 carbon atoms, cycloalkyl having 3 to 8 carbon atoms, bicycloalkyl having 7 to 12 carbon atoms, phenyl which is optionally mono- to trisubstituted by identical or different substituents selected from the group consisting of halogen and alkyl having 1 to 4 carbon atoms or represents phenylalkyl having 1 to 4 carbon atoms in the alkyl moiety which is optionally mono- to trisubstituted by identical or different substituents selected from the group consisting of halogen and alkyl having 1 to 4 carbon atoms, and
- n represents the numbers 0, 1, 2 or 3, or two vicinal $R^2$ radicals together represent an alkylene chain having 3 or 4 carbon atoms.

2. A microbicidal composition comprising a microbicidally effective amount of a compound as claimed in claim 1 and an inert diluent.

3. A method of controlling undesired microorganisms in plant protection and in the preservation of materials, which method comprises applying to such undesired microorganisms or to their habitat a microbicidally effective amount of a compound as claimed in claim 1.

4. A process for preparing a 1,3-dimethyl-5-fluoro-pyrazol-4-carboxamide of the formula (I) according to claim 1, comprising the step of reacting 1,3-dimethyl-5-fluoro-pyrazol-4-carbonyl halides of the formula

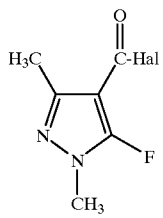

(II)

in which
Hal represents fluorine, chlorine or bromine, with an amine of the formula $H_2N-R$     (III)

in which
R is defined as in claim 1, if appropriate in the presence of an acid binder and if appropriate in the presence of a diluent.

* * * * *